(12) United States Patent
Takino et al.

(10) Patent No.: US 8,771,449 B2
(45) Date of Patent: Jul. 8, 2014

(54) METHOD FOR MAKING DISPOSABLE DIAPER

(75) Inventors: Shunsuke Takino, Kagawa (JP); Yuki Maeda, Kagawa (JP); Hiroyuki Tanji, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 459 days.

(21) Appl. No.: 12/676,614

(22) PCT Filed: Jul. 11, 2008

(86) PCT No.: PCT/JP2008/062552
§ 371 (c)(1),
(2), (4) Date: Jun. 7, 2010

(87) PCT Pub. No.: WO2009/031359
PCT Pub. Date: Mar. 12, 2009

(65) Prior Publication Data
US 2010/0252178 A1    Oct. 7, 2010

(30) Foreign Application Priority Data

Sep. 5, 2007    (JP) .................................. 2007-230639

(51) Int. Cl.
*A61F 13/15* (2006.01)
(52) U.S. Cl.
CPC ..... *A61F 13/15593* (2013.01); *A61F 13/15804* (2013.01)
USPC ........... 156/161; 156/178; 156/204; 156/226; 156/229

(58) Field of Classification Search
None
See application file for complete search history.

(56) References Cited

U.S. PATENT DOCUMENTS

| 6,447,628 B1* | 9/2002 | Couillard et al. ............. 156/204 |
| 2004/0112508 A1 | 6/2004 | Umebayashi et al. |
| 2004/0182502 A1* | 9/2004 | Wagner et al. ............... 156/204 |
| 2004/0243083 A1 | 12/2004 | Matsuda et al. |
| 2006/0244166 A1* | 11/2006 | Wada et al. .................. 264/37.1 |

(Continued)

FOREIGN PATENT DOCUMENTS

| JP | 03176053 | 7/1991 |
| JP | 2004-033549 | 2/2004 |

(Continued)

OTHER PUBLICATIONS

ISR for PCT/JP2008/062552, mailed Oct. 14, 2008.

(Continued)

*Primary Examiner* — Barbara J Musser
(74) *Attorney, Agent, or Firm* — Lowe Hauptman & Ham LLP

(57) ABSTRACT

The present invention aims to provide a method for making disposable diapers so improved that no displacement of the absorbent core from the middle between a pair of the leg elastic members. The method comprises the step P1 of bonding under tension elastic members to webs continuously fed in a machine direction MD to form front and rear sheet members the step P2 of bonding an absorbent panel provided along opposite long sides of a rectangle with a pair of elastic members for a crotch region and including an absorbent core bonded thereto so as to be symmetric about an imaginary center line bisecting a distance between a pair of the elastic members for the crotch region to the front and rear sheet members at regular intervals and the step P3 of cutting the front and rear sheet members.

18 Claims, 6 Drawing Sheets

(56) References Cited

U.S. PATENT DOCUMENTS

2006/0254708 A1 11/2006 Wada et al.
2007/0038198 A1* 2/2007 Wada ..................... 604/385.3
2008/0027406 A1 1/2008 Shirai et al.

FOREIGN PATENT DOCUMENTS

| | | | |
|---|---|---|---|
| JP | 2004187873 | | 7/2004 |
| JP | 2004329873 A | | 11/2004 |
| JP | 2005021196 A | * | 1/2005 |
| JP | 2006149745 A | | 6/2006 |
| JP | 2006525858 | | 11/2006 |
| WO | 2005044167 A1 | | 5/2005 |
| WO | WO 2005044168 A1 | * | 5/2005 |
| WO | 2005094746 A1 | | 10/2005 |

OTHER PUBLICATIONS

Supplementary European Search Report issued in EP 08778068.0 dated Nov. 26, 2012, 7 pages.

* cited by examiner

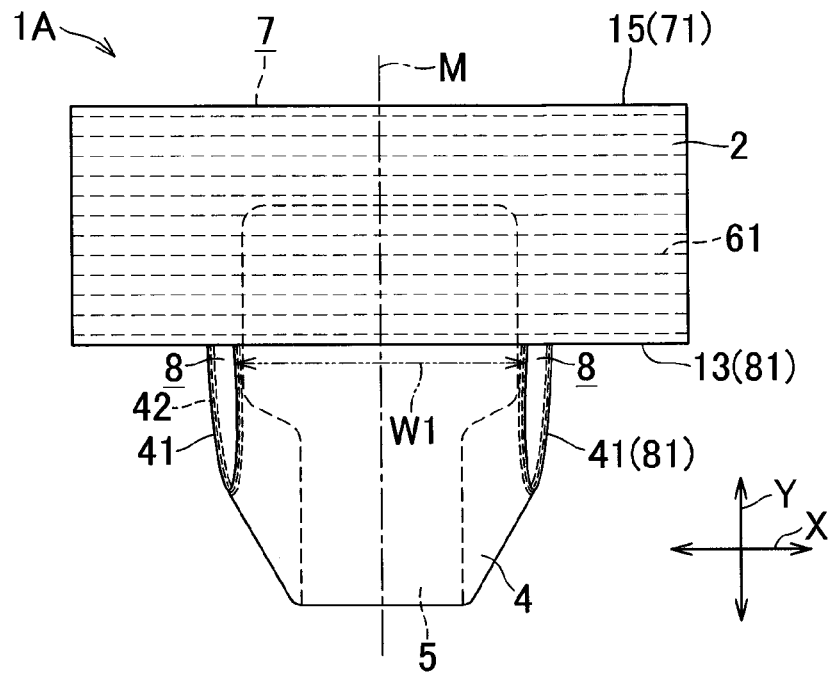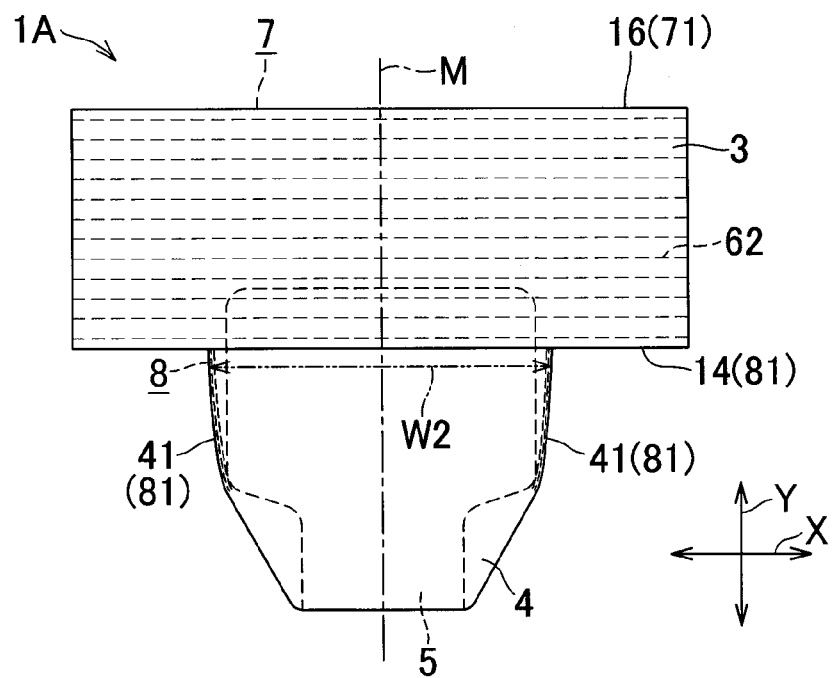

METHOD FOR MAKING DISPOSABLE DIAPER

RELATED APPLICATIONS

The present application is national phase of PCT/JP2008/062552 filed Jul. 11, 2008, and claims priority from Japanese Application Number 2007-230639, filed Sep. 5, 2007, the disclosures of which are hereby incorporated by reference herein in their entirety.

TECHNICAL FIELD

The present invention relates to a method for making disposable diaper.

RELATED ART

Disposable diapers, in general, are provided along regions in which a diaper comes in contact with the wearer's waist and legs with waist elastic members and leg elastic members. For example, PATENT DOCUMENT 1 discloses a method for making a disposable diaper as illustrated in FIG. 7 of the accompanying drawings, comprising the step S-1 of feeding a first web 115 and a second web 116 both previously provided with leg elastic members 125 bonded thereto and waist elastic members 124 in a machine direction, the step S-2 of attaching the waist elastic members 124 to the first and second webs 115, 116 and then bonding the first and second webs 115, 116 to each other and the step S-3 of attaching an absorbent panel 103 containing an absorbent core 128 to the first web 115 so as to be positioned between a pair of the leg elastic members 125.

PATENT DOCUMENT 1: Japanese Unexamined Patent Application Publication No. 2004-187873

DISCLOSURE OF THE INVENTION

Problem to be Solved by the Invention

On the conventional production line such as disclosed in PATENT DOCUMENT 1, a long sheet such as the first web 115 is fed in the machine direction and the elastic members such as the waist elastic members 124 are bonded under tension to such long sheet. Consequentially, a tension in a direction opposite to the machine direction is exerted upon the long sheet and it is inevitable that, when the production line is temporarily stopped for some reason, the long sheet on the production line is displaced from the position at the moment of such temporary stop of the production line in the direction opposite to the machine direction. If the production of diaper is started again disregarding this displacement, the position of the absorbent panel 103 will be necessarily displaced from the middle between each pair of the leg elastic members in each of the diapers output thereafter.

Thus the production line will output a number of off-specification diapers in each of which the absorbent core 128 is asymmetric about an imaginary center line bisecting a distance between a pair of the leg elastic members 125 and, in consequence, a pair of the leg elastic members 125 and/or the absorbent core 128 can not be properly positioned in the wearer's crotch region. To avoid such problem, the method of prior art has been required to readjust the accurate relationship between the long sheet and the position at which the absorbent panel 103 should be attached to the long sheet with manual operation.

In view of the problem as has been described above, it is an object of the present invention to provide a method for making the diaper so improved that no displacement of the absorbent core from the middle between a pair of the leg elastic members even when the production line is temporarily stopped.

Measure to Solve the Problem

A method for making disposable diaper according to the present invention comprises the steps of continuously feeding elastic members for a front sheet member and elastic members for a rear sheet member in parallel to each other under tension in a first machine direction and bonding these elastic members to webs of the front and rear sheet members, respectively, continuously fed in the first machine direction and thereby forming the front sheet member having a constant width dimension as measured in a direction orthogonal to the first machine direction and the rear sheet member also having a constant width dimension so that the front and rear sheet members may continuously run with a spacing from and in parallel to each other, feeding at regular intervals an absorbent panel provided along opposite long sides with a pair of elastic members for a crotch region bonded under tension thereto and provided with an absorbent core bonded thereto so as to be symmetric about an imaginary center line bisecting a distance between the pair of elastic members for the crotch region to the front and rear sheet members running in the first machine direction, placing and bonding the absorbent panel on and to the front and rear sheet members so that the pair of elastic members for the crotch region extend orthogonally to the elastic members for the front sheet member and the elastic members for the rear sheet member, and cutting the front and rear sheet members having the absorbent panel bonded thereto substantially along the middle between each pair of the adjacent absorbent panels to obtain individual diapers.

According to one preferred embodiment, the method further comprising the steps of continuously feeding a liquid-pervious sheet, a liquid-impervious sheet and the pair of elastic members for the crotch region in a second machine direction and feeding the absorbent core at regular intervals so as to be symmetric about the imaginary center line bisecting the distance between the pair of elastic members for the crotch region, bonding the elastic members for the crotch region under tension to at least one of the liquid-pervious sheet and the liquid-impervious sheet and bonding the absorbent core between the liquid-pervious sheet and the liquid-impervious sheet, and cutting the liquid-pervious sheet and the liquid-impervious sheet substantially along the middle between each pair of the adjacent absorbent cores in a direction orthogonal to the second machine direction to obtain the individual absorbent panels.

The method according to the present invention for making disposable diaper includes the other preferred embodiments as will be described below.

The step of forming the sheet members comprises the step of bonding the elastic members for the front sheet member and the elastic members for the rear sheet member under tension to the front sheet member and the rear sheet member, respectively, so that the front sheet member may contract more significantly than the rear sheet member when the elastic members for the front and rear sheet members, respectively, have tension released. Alternatively, the step of forming the sheet members comprises the step of adjusting a tensile stress under which the elastic members for the front sheet member are bonded to the front sheet member to be higher than a tensile stress under which the elastic members for the rear sheet member are bonded to the rear sheet member.

The method may further comprise the step of making the elastic members for the rear sheet member inelastic at least in a region of these elastic members overlapped by the absorbent core.

Furthermore, the step of bonding may comprise the step of bonding the absorbent panel to the front sheet member and the rear sheet member so that a longitudinal dimension over which the absorbent core overlaps the front sheet member is larger than a longitudinal dimension over which the absorbent core overlaps the rear sheet member.

Effect of the Invention

According to the method according to the present invention for making the disposable diapers, the absorbent panel previously provided with the absorbent core bonded thereto so that a pair of the elastic members for the crotch region may be symmetric about this absorbent core. Such measure reliably prevents the absorbent core from displaced with respect to the middle between a pair of the leg elastic members. In addition, the method according to the present invention allows it to obtain the diaper free from any displacement of the absorbent panel with respect to the front and rear sheet members since the construction of the front and rear sheet members as viewed in the first machine direction is constant.

BRIEF DESCRIPTION OF THE DRAWINGS

FIG. 5 is a front view of the diaper as viewed from a side of a ventral belt.
FIG. 6 is a rear view of the diaper as viewed from a side of a dorsal belt.

DESCRIPTION OF THE BEST MODE FOR WORKING OF THE INVENTION

Figure 1:
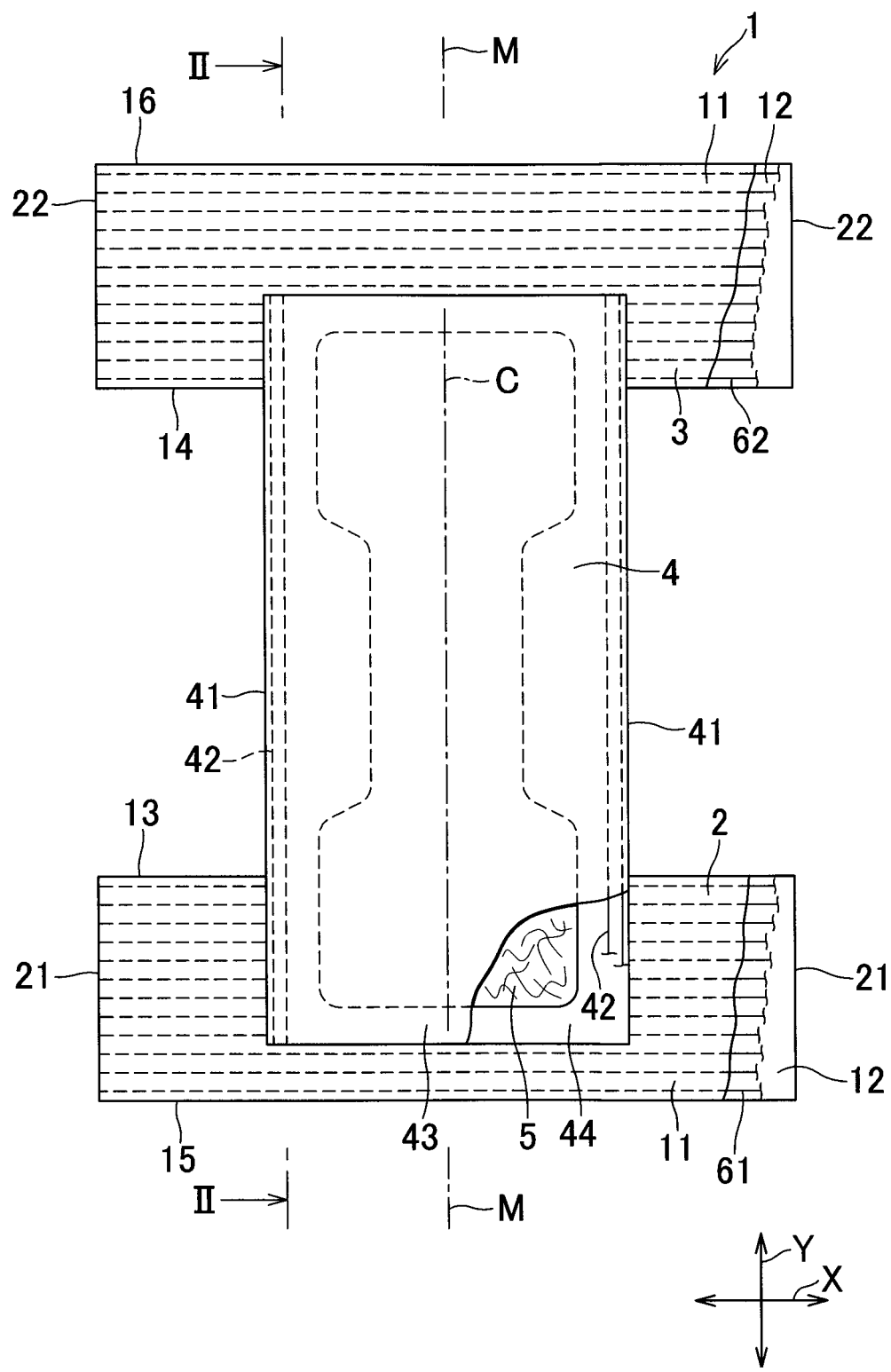
FIG. 1 is a plan view showing a diaper as flatly developed.
Figure 2:
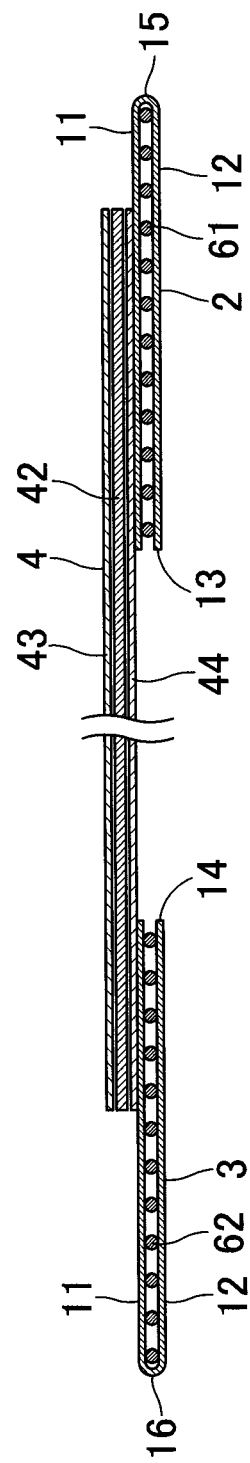
FIG. 2 is a sectional view taken along the line II-II in FIG. 1.
Figure 3:
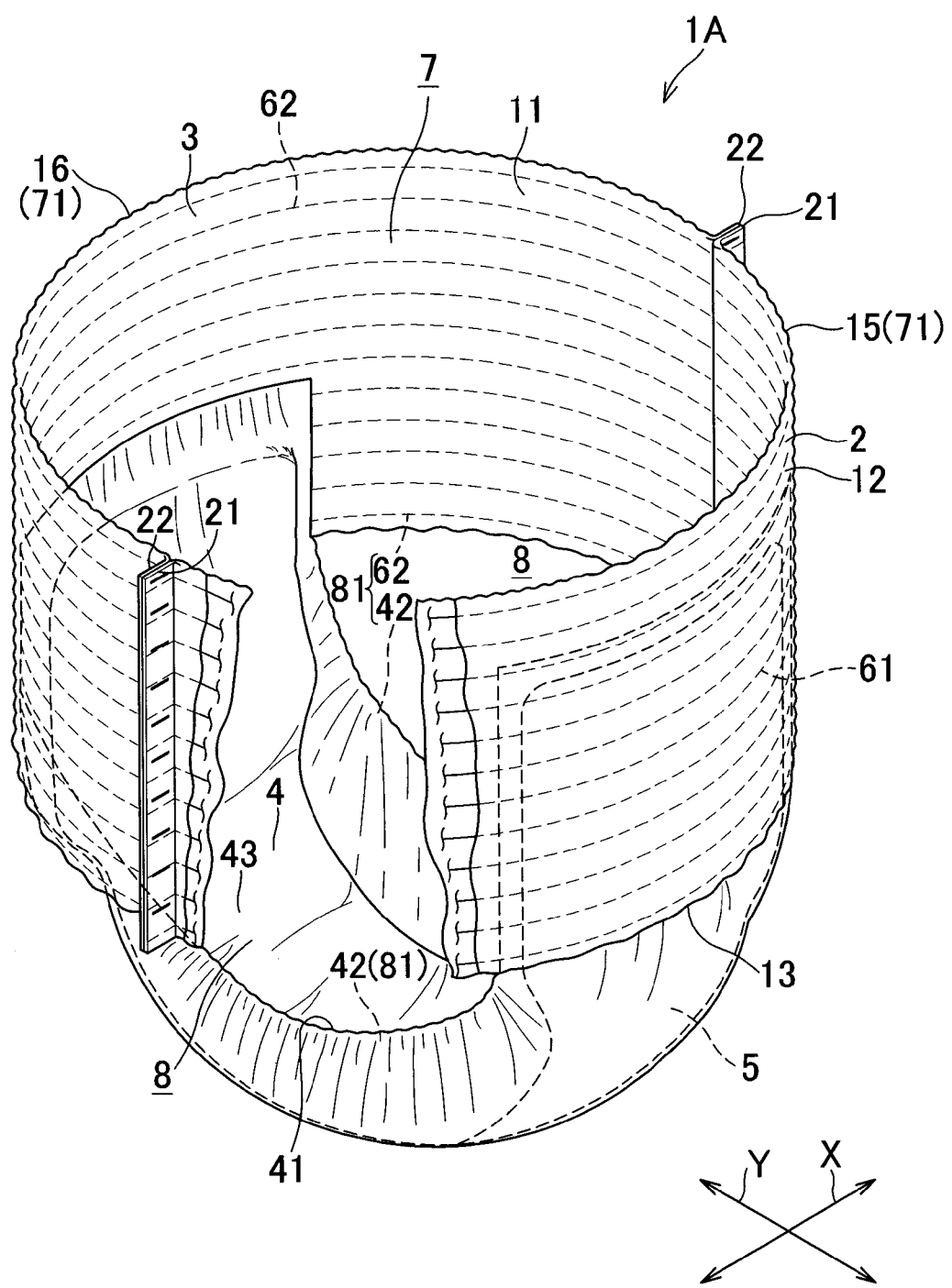
FIG. 3 is a perspective view of the diaper shaped in a pant.

First of all, a diaper 1 according to the present invention will be described with reference to FIGS. 1 through 3. FIG. 1 is a plan view showing the diaper 1 flatly developed and as viewed from a side thereof facing the wearer's skin, FIG. 2 is a sectional view taken along the line II-II in FIG. 1 and FIG. 3 is a partially cutaway perspective view showing the diaper 1 shaped in a pant.

The diaper 1 comprises a rectangular front waist region-side belt 2 extending in a transverse direction indicated by an arrow X, a rectangular rear waist region-side belt 3 spaced from and extending in parallel to the front waist region-side belt 2 in the transverse direction and a rectangular absorbent panel 4 extending in a longitudinal direction indicated by an arrow Y and put flat and bonded together with the front waist region-side belt 2 as well as the rear waist region-side belt 3 so as to connect these two belts 2, 3 to each other. The absorbent panel 4 has a transverse dimension smaller than those of the front waist region-side belt 2 and the rear waist region-side belt 3 and includes an absorbent core 5. The diaper 1 substantially has an I-shape which is substantially symmetric about a longitudinal center line M bisecting a transverse dimension of the diaper 1. The absorbent panel 4 is bonded to the front and rear region-side belts 2, 3 approximately in respective middle zones thereof so that the absorbent panel 4 also is symmetric about the longitudinal center line M.

Each of the front waist region-side belt 2 and the rear waist region-side belt 3 comprises a topsheet 11 and a backsheet 12 being same in shape as well as in size, between which a plurality of elastic members 61 for the front waist region-side belt 2 or a plurality of elastic members 62 for the rear waist region-side belt 3 are sandwiched and intermittently bonded under tension in the transverse direction X to these sheets 11, 12 by means of hot melt adhesive (not shown). The front waist region-side belt 2 and the rear waist region-side belt 3 extend in parallel to each other and orthogonally to the longitudinal center line M. Both the elastic members 61 for the front waist region-side belt 2 and the elastic members 62 for the rear waist region-side belt 3 comprise a plurality of rubber strings regularly spaced one from another in the longitudinal direction Y over entire areas of the respective belts 2, 3. It will be appreciated that the topsheet 11 faces the wearer's skin and the backsheet 12 faces away from the wearer's skin with the diaper 1 in use.

The rectangular absorbent panel 4 comprises a rectangular liquid-absorbent sheet 43 and a rectangular liquid-impervious sheet 44 both being larger than the rectangular absorbent core 5 at least in the transverse dimension thereof, the rectangular absorbent core 5 sandwiched between these sheets 43, 44, elastic members 42 extending in the longitudinal direction fully along opposite side edges 41, 41 of the crotch region defined by opposite side edges of the rectangular absorbent panel 4 and intermittently bonded to those sheets 43, 44. The elastic members 42 on both side edges of the crotch region are bonded to those sheets 43, 44 by means of hot melt adhesive (not shown). In this particular embodiment, rubber strings are used as the elastic members 42 on both side edges of the crotch region. It will be appreciated that the liquid-pervious sheet 43 faces the wearer's skin and the liquid-impervious sheet 44 facing away from the wearer's skin with the diaper 1 in use.

The absorbent core 5 is contained within the absorbent panel 4 so as to be symmetric about an imaginary center line C bisecting a distance between the elastic members 42 extending along the opposite side edges of the crotch region. The imaginary center line C falls on the longitudinal center line with the absorbent panel 4 bonded to the front waist region-side belt 2 and the rear waist region-side belt 3. Here again, it will be appreciated that the liquid-pervious sheet 43 faces the wearer's skin and the liquid-impervious sheet 44 faces away from the wearer's skin with the diaper 1 in use.

Preferably, the absorbent core 5 is positioned to the front waist region-side belt 2 and the rear waist region-side belt 3 are bonded to so that a longitudinal dimension over which the absorbent core 5 overlaps the front waist region-side belt 2 is larger than a longitudinal dimension over which the absorbent core 5 overlaps the rear waist region-side belt 3, as will be apparent from FIG. 1. It is assured thereby that an effective area of the absorbent core 5 to cover a front region of the wearer's crotch extending aside toward the front waist region-side belt 2 is sufficiently large to absorb urine with a high efficiency.

The absorbent panel 4 is put flat and bonded to the front waist region-side belt 2 and the rear waist region-side belt 3 so as to overlap respective regions of these belts 2, 3 in which the elastic members 61, 62 are present. In consequence, the elastic members 61 for the front waist region-side belt 2, the elastic members 62 for the rear waist region-side belt 3 and the elastic members 42 for the crotch region overlap one another in the regions wherein the absorbent panel 4 overlaps the front waist region-side belt 2 and the rear waist region-side belt 3, as will be apparent from FIG. 2.

Both the elastic members 61 for the front waist region-side belt and the elastic members 62 for the rear waist region-side belt 3 are bonded to the respective belts 2, 3 by means of hot melt adhesive (not shown) while the elastic members 42 for the crotch region are bonded to the absorbent panel 4. It means that the elastic members 42 for the crotch region are linked with the elastic members 61 for the front waist region-side belt and the elastic members 62 for the rear waist region-side belt through the intermediary of the topsheet 11 and the liquid-impervious sheet 44. Consequentially, a stretching force exerted on any one of these elastic member groups causes the other elastic member groups also to be responsive to such stretching force and to be stretched.

Materials for the liquid-pervious sheet 43 and the liquid-impervious sheet 44 constituting the absorbent panel may be appropriately selected in consideration of the required properties such as liquid permeability, air permeability and soft touch from various types of fibrous nonwoven fabrics and/or films conventionally used for the disposable diaper and made of thermoplastic synthetic resins. As the absorbent core 5, body fluid absorbent materials of well known art containing fluff pulp may be used. The absorbent core 5 is wrapped with tissue paper (not shown) and bonded to the liquid-pervious sheet 43 and the liquid-impervious sheet 44.

The topsheet 11 and the backsheet 12 constituting the front waist region-side belt 2 and the rear waist region-side belt 3 also may be appropriately selected from various types of fibrous nonwoven fabrics and/or films made of thermoplastic synthetic resins. The material for the topsheet 11 may be the same as or different from the material for the backsheet 12. Furthermore, a single sheet may be folded in two so that the one half defines the topsheet 11 and the other half defines the backsheet 12.

The elastic members 42 for the crotch region and the waist elastic members 61, 62 may be provided in the form of rubber strings, tape- or ribbon-shaped vulcanized rubber, thermoplastic elastomer, elasticized nonwoven fabrics or resin films. Bonding among the respective sheets, the respective elastic members, and the body fluid absorbent members may be carried out using the method well known in the field of the disposable diaper, for example, adhesion with hot melt adhesive or heat sealing.

By joining opposite side edges 21, 21 of the front waist region-side belt 2 extending in the longitudinal direction to opposite side edges 22, 22 of the rear waist region-side belt 3 extending in the longitudinal direction so that the front waist region-side belt 2 and the rear waist region-side belt 3 may be bowed so as to define an annulus, the diaper 1 is shaped in a pant as shown in FIG. 3. It is also possible to connect the opposite side edges 21, 21 of the front waist region-side belt 2 with the opposite side edges 22, 22 of the rear waist region-side belt 3 not by bonding these side edges in the manner as seen in FIG. 3 but through the intermediary of a so-called mechanical fastener consisting of a hook member and a loop member or by means of a pressure-sensitive adhesive tape/a target tape, although these alternative methods are not illustrated.

Having been shaped in a pant as shown in FIG. 3, the diaper 1A has a waist-opening 7 defined by the front waist region-side belt 2 and the rear waist region-side belt 3 annularly joined together, and a pair of leg-openings 8 defined by the front waist region-side belt 2, the rear waist region-side belt 3 and the absorbent panel 4 bonded to these belts 2, 3. More specifically, referring to FIG. 1, the pair of leg-openings 8 is defined by an inner edge 13 of the front waist region-side belt 2 and a inner edge 14 of the rear waist region-side belt 3 both extending in the transverse direction and opposed to each other across the absorbent panel 4 cooperating with the opposite side edges 41 of the absorbent panel 4, i.e., of the crotch region. A peripheral edge of the waist-opening 71 is defined by an outer edge 15 of the front waist region-side belt 2 and an outer edge of the rear waist region-side belt 3 both extending in the transverse direction in parallel to the respective inner edges 13, 14.

As has previously been described, the elastic members are linked with the elastic members 61 for the front waist region-side belt and the elastic members 62 for the rear waist region-side belt. Furthermore the elastic members 61 for the front waist region-side belt 2 and the elastic members 62 for the rear waist region-side belt 3 are also linked with each other as the front waist region-side belt 2 and the rear waist region-side belt 3 are annularly joined to each other. In the pant-type diaper 1A, therefore, the elastic members 61 for the front waist region-side belt extending in the vicinity of the inner edge 13 of the front waist region-side belt, the elastic members 62 for the rear waist region-side belt extending in the vicinity of the inner edge of the rear waist region-side belt and a pair of the elastic members 42 for the crotch region are annularly linked one with another along the leg-openings 8 and function as leg elastic members 81.

The absorbent core 5 is placed in the absorbent panel 4 so as to be symmetric about the imaginary center line C bisecting a pair of the elastic members 42 partially defining the leg elastic members 81. In consequence, it is ensured that the absorbent core 5 can be placed in the middle between the pair of leg elastic members 81 no matter how the absorbent panel 4 is bonded to the front waist region-side belt 2 and the rear waist region-side belt 3. In other words, by providing the absorbent panel 4 with the pair of elastic members 42 for the crotch region partially constituting the leg elastic members 81, it is ensured that the absorbent core is always placed in the middle between the leg elastic members 81.

Now a method for making the diaper 1 according to the present invention will be described with reference to FIG. 4 which is a schematic diagram illustrating the steps followed to make the target article.

Figure 4:
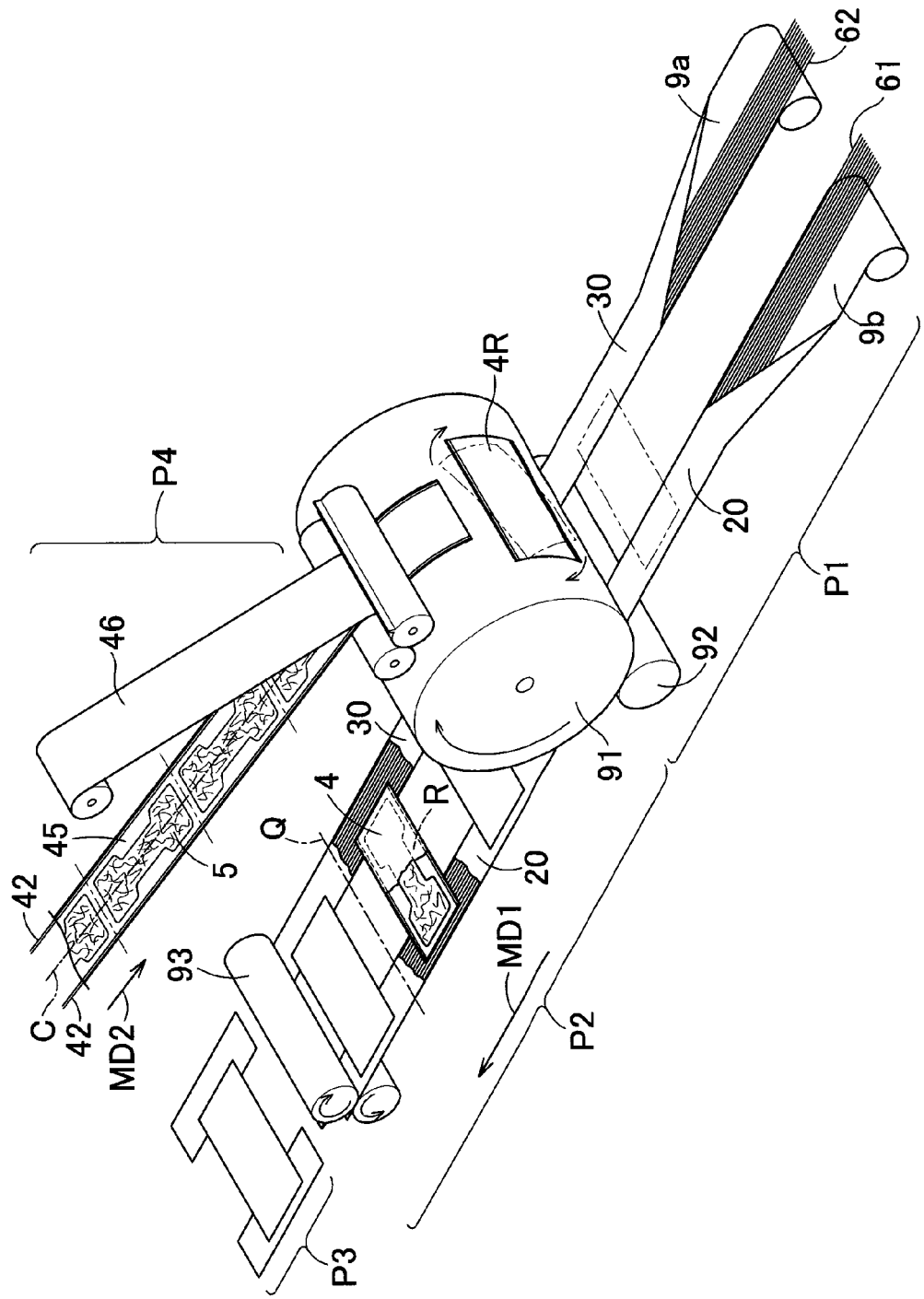
FIG. 4 is a schematic diagram illustrating the method for making the diaper.
Figure 7:
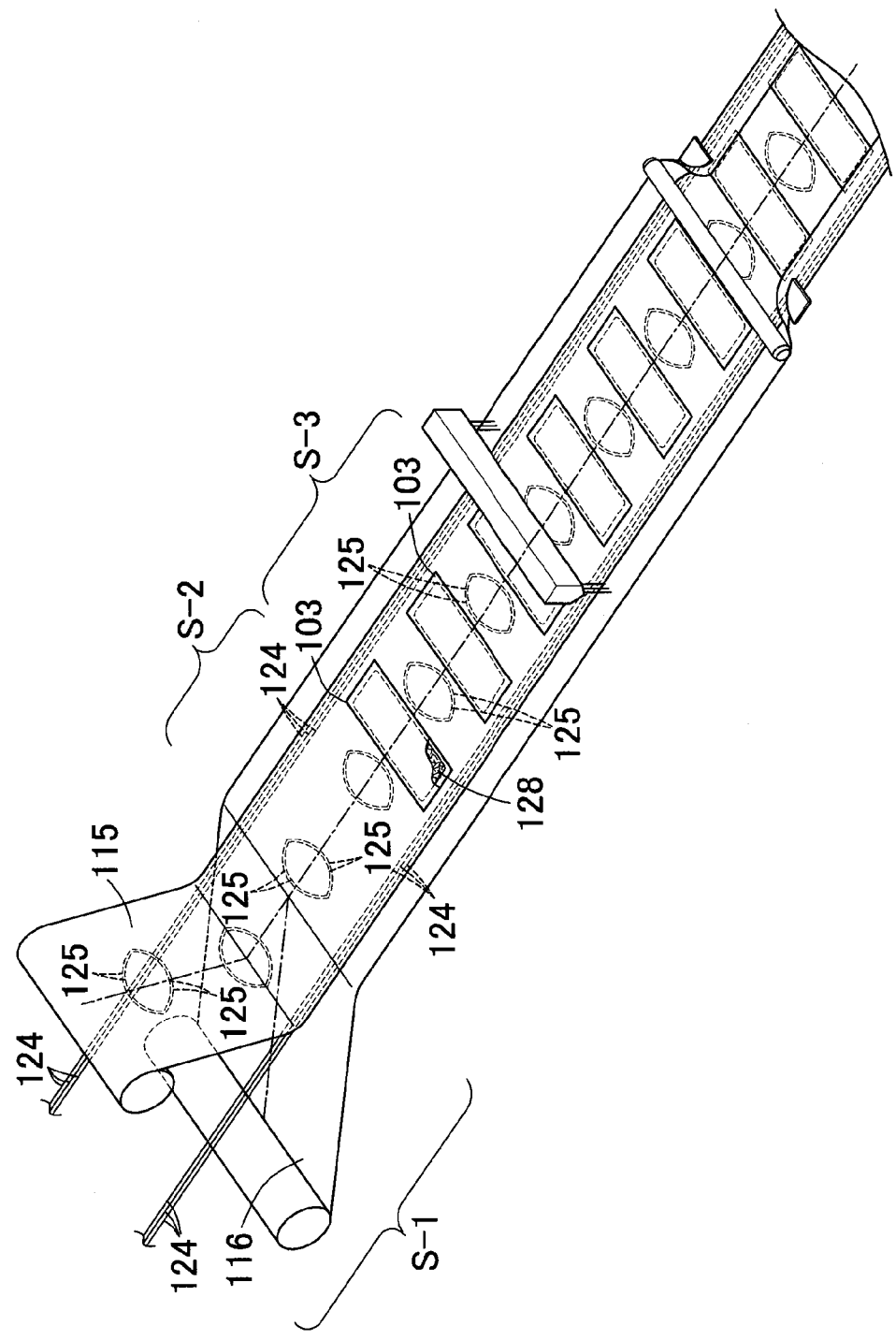
FIG. 7 is a schematic diagram exemplarily illustrating the method of prior art for making the diaper.

In the step P1 of forming sheet members, according to an embodiment illustrated by FIG. 4, a web 9a to be handled to form a front waist region sheet member 20 and a web 9b to be handled to provide a rear waist region sheet member 30 are continuously fed in a first machine direction MD1. These webs 9a, 9b are respectively coated with hot melt adhesive by not shown coaters and then the elastic members 61, 62 for the front and rear region-side belts continuously fed in the first machine direction under a given tension are bonded to each of the webs 9a, 9b over approximately half width thereof as viewed in a direction (indicated by an arrow CD) orthogonal to the first machine direction. The elastic members 61, 62 for the front and rear region-side belts may respectively comprise a plurality of rubber strings wherein the rubber strings may be regularly or irregularly spaced one from another.

Then, the webs 9a, 9b are folded in two, respectively, so that the surfaces thereof having the elastic members 61, 62 for the front and rear region-side belts coated thereon define inner surfaces. In this way, the front waist region sheet member 20 having a constant transverse dimension and provided with the elastic members 61 is obtained and at the same time the rear waist region sheet member 30 having a constant transverse dimension and provided with the elastic members 62 is obtained. Thus, both the front waist region sheet member 20 and the rear waist region sheet member 30 respectively have constant structures as viewed in the first machine direction. It should be noted that the transverse dimensions of the front and rear waist region sheet members 20, 30 may be same or different. Actual transverse dimensions of these sheet members 20, 30 may be appropriately selected from a range of about 50 to about 250 mm. The front and rear waist region sheet members 20, 30 formed in this manner are spaced from and in parallel to each other in the transverse direction and fed in this relationship to the step P2 of bonding.

In the step P2 of bonding, the absorbent panels 4 each containing the absorbent core 5 are fed at regular intervals toward the front and rear sheet members 20, 30 running in the first machine direction and bonded to these sheet members 20, 30. To feed the absorbent panels 4 at regular intervals, a combination of an angle-convertible roll 91 and a press roll 92 as disclosed in Japanese Unexamined Patent Application Publication No. 2004-33549 may be used. Specifically, the absorbent panel is 90° C. turned by the angle-convertible roll 91 and overlapped on the front sheet member 20 and the rear sheet member 30 with the crotch region elastic members 42, 42 of the absorbent panel 4 extending orthogonally to the elastic members 61, for the front and rear waist region-side belts, respectively. Preferably, the absorbent panel 4 is bonded to the front and rear sheet members 20, 30 so that a longitudinal dimension of the absorbent panel 4 overlapping front sheet member 20 is larger than a longitudinal dimension of the absorbent panel 4 overlapping the rear sheet member 30. The front and rear sheet members 20, 30 having the absorbent panel 4 bonded thereto in this manner are fed to the step P3 of cutting. However, before the step P3 of cutting is described in details, the step P4 of forming the absorbent structure will be described.

The step P4 of forming the absorbent panels 4 is a step which is a separate step rather than a step linearly contiguous to the step P1 of forming the sheet members and the step P2 of bonding. The step P4 of forming the absorbent panels 4 may be linearly connected between the steps P1 and P2 or the individual absorbent panels 4 formed in the off-line step P4 may be fed at regular intervals to the front and rear sheet members 20, 30.

In the step P4 of forming the absorbent panel, the liquid-pervious sheet 45 and the liquid-impervious sheet 46 continuously fed in a second machine direction indicated by an arrow MD2 are coated on one of opposed surfaces thereof with hot melt adhesive by means of a not illustrated coater, then a pair of the elastic members 42, 42 for the crotch region extending in parallel to each other are continuously fed under tension in the second machine direction to the surface of the sheet 45 or 46 coated with hot melt adhesive and the absorbent cores 5 are fed at regular intervals so as to be placed between each pair of the elastic members 42 for the crotch region.

Then, the absorbent core 5 and each pair of the elastic members 42 for the crotch region are adhesively fixed between the liquid-pervious sheet 45 and the liquid-impervious sheet 46 under a pressure exerted by a roll or the like and thereafter cut substantially along a middle line of each pair of the adjacent absorbent cores 5 in a direction orthogonal to the second machine direction to obtain individual rectangular absorbent panels 4. Each pair of the elastic members 42 for the crotch region extend along opposite long sides of the rectangular absorbent panel 4.

The absorbent core 5 is bonded between the liquid-pervious sheet 45 and the liquid-impervious sheet 46 so that the absorbent core 5 is symmetric about the imaginary center line C bisecting the distance between a pair of the elastic members 42 for the crotch region. In this way, there is no possibility that the position of the absorbent core 5 might be displaced from the middle of a pair of the leg elastic members 81 no matter how the absorbent panel 4 is bonded to the front and rear sheet members 20, 30 and no matter whether a temporary stop of the production line occurs or not. It should be noted here that an essential condition required for the elastic members 42 for the crotch region is to extend along the opposite long sides of the rectangular absorbent panel 4 and it is not essential for these elastic members 42 to be bonded to both the liquid-pervious sheet 45 and the liquid-impervious sheet 46. Specifically, it is possible without departing from the scope of the invention to bond these elastic members 42 to any one of the liquid-pervious sheet 45 and the liquid-impervious sheet 46.

In the step P3 of cutting following the step P2 of bonding, a set of well known cutting rolls 93 having upper and lower cutter blades and operating to cut the front and rear sheet members 20, 30 at regular intervals may be used. More specifically, these sheets 20, 30 are cut substantially along the middle between a pair of the adjacent absorbent panels 4 in the width direction to obtain the individual diapers 1. In the individual diaper 1, the front and rear sheet members 20, 30 respectively define the front waist region-side belt 2 and the rear waist region-side belt 3. The opposite side edges 21, 21 of the front waist region-side belt 2 are bonded to the opposite side edges 22, 22 of the rear waist region-side belt 3 to obtain the pant-type diaper 1. It is also possible, as has previously been described, the opposite side edges 21, 21 and the opposite side edges 22, 22 may be provided with tape fasteners by means of which the front and rear waist regions may be connected to each other and thereby to obtain the pant-type diaper 1.

Even if the production line is temporarily stopped during these steps and the front and rear sheet members 20, are pulled in a direction opposite to the first machine direction under tension of the elastic members 61, 62 for the front and rear waist region-side belts 2, 3 not bonded to the front and rear sheet members 20, 30, as a result, even if a region R in which the absorbent panel 4 was to be bonded to the sheet member and an imaginary cut line Q along which the front and rear sheet members 20, 30 were to be cut will be displaced in the direction opposite to the first machine direction by a same distance, there is no problem due to the following reason.

Upon starting again of the production line, the diapers 1 are produced on the basis of new bonding region R and new imaginary cut line Q both differing from those before the production line has temporarily stopped and it is ensured that the diaper 1 free from any displacement of the absorbent panel 4 with respect to the front and rear sheet members 20, 30 can be obtained since the construction of the front and rear sheet members 20, 30 as viewed in the first machine direction is constant.

If any displacement of the absorbent panel 4 with respect to the front and rear sheet members occurs during use of the method according to the present, such displacement is limited to a region in which the absorbent panel 4 has bonded to the sheet member in the step P2 and still not cut in the step P3. Therefore there is no possibility that a number of the diapers 1 in each of which the absorbent panel 4 and the absorbent core 5 are out of the normal positions as the prior art has been the case.

Furthermore, even if any displacement of the absorbent panel 4 with respect to the front and rear sheet members 20, 30 occurs, it is not apprehended that any displacement of the absorbent core 5 with respect to the leg elastic members 81 might occur as the prior art has been the case. During a temporary stop of the production line, the front and rear sheet members 20, 30 may be fixedly clipped between the angle-convertible roll 91 and the press roll 92 in the step P3 of bonding as well as between the pair of cutting rolls 93 in the step P3 of cutting to prevent these sheet members 20, 30 from moving in the direction opposite to the first machine direction and thereby to prevent the absorbent panel 4 from being displaced with respect to the front and rear sheet members 20, 30. In this way, undesirable output of the diaper 1 involving a displacement of the absorbent panel 4 can be more reliable avoided.

While the sheet member forming the step P1 has been described above on the embodiment wherein the front and rear sheet members 20, 30 are formed from two webs 9a, 9b, it is possible to implement the step P1 in a manner as follows: after a plurality of rubber strings have been bonded under tension to a single web being fed in the first machine direction, the web is folded in two so as to cover these rubber strings, then the folded web is continuously cut in a direction parallel to the first machine direction to obtain the front and rear sheet members 20, 30 and these sheet members 20, 30 are spaced from each other in the width direction so as to run in parallel to each other. It is also possible to implement the step P1 in a manner as follows: a pair of webs respectively prepared to form the front and rear sheet members 20, 30 spaced from each other in the width direction are fed in parallel to each other in the first machine direction, a plurality of rubber strings are bonded under tension to the respective webs and then a pair of separately fed webs are respectively placed on the webs provided with a plurality of rubber strings bonded thereto so as to cover these rubber strings and thereby to form the front and rear sheet members 20, 30.

No matter which embodiment of the step 1 is adopted to form the front and rear sheet members 20, 30, it is desired to bond the elastic members 61, 62 for the front and rear sheet members under tension so that the front sheet member may contract more significantly than the rear sheet member 30 when the elastic members 61 for the front waist region-side belt and the elastic members 62 for the rear waist region-side belt have tension released. Configuration of the diaper 1A obtained by bonding of the elastic members 61, 62 for the front and rear waist region-side belts are schematically illustrated in FIGS. 5 and 6. FIG. 5 is a view of the diaper 1A as viewed from the side of the front waist region-side belt 2 and FIG. 6 is a view of the diaper 1A as viewed from the side of the rear waist region-side belt 3.

The front waist region-side belt 2 contracts more significantly than the rear waist region-side belt 3 in the diaper 1A since the front sheet member 20 contracts more significantly than the rear sheet member 30. In consequence, an apparent width W1 of the absorbent panel 4 of the diaper 1A in the vicinity of a boundary line between the absorbent panel 4 and the front waist region-side belt is smaller than an apparent width W2 of the absorbent panel 4 in the vicinity of a boundary line between the absorbent panel 4 and the rear waist region-side belt 3.

The configuration of the absorbent panel 4 such that the apparent width thereof is gradually reduced from the rear waist region-side belt 3 to the front waist region-side belt 2 advantageously ensures that the diaper 1A can cover a wide range of the wearer's buttock and prevent the wearer from experiencing an uncomfortable feeling to wear due to the sheets becoming bulky in the wearer's crotch region. In addition, the pair of leg-openings defined by the absorbent panel 4 and the annularly connected front and rear region-side belts 2, 3 open somewhat forwardly so as to improve a fit of the diaper 1A around the wearer's legs.

One of methods enabling the front sheet member 20 to contract more significantly than the rear sheet member 30 is to adjust a tensile stress of the elastic members 61 for the front waist region-side belt under which these elastic members 61 are bonded to the front sheet member 20 to be higher than a tensile stress under which the elastic members 62 for the rear waist region-side belt are bonded to the rear sheet member 30. Specifically, a stretching percentage under which the elastic members 61 are bonded to the front sheet member 20 is adjusted to be higher than a stretching percentage under which the elastic members 62 are bonded to the rear sheet member 30 on the assumption that both the elastic members 61, 62 are same in quality of material as well as in configuration.

Alternatively, the elastic members 61 for the front sheet member 20 may be formed by much more number of rubber strings than the rubber strings constituting the elastic members 62 for the rear sheet member 30. It is also possible to differentiate material quality and/or configuration of the rubber strings between the elastic members 61 for the front sheet member 20 and the elastic members 62 for the rear sheet member 30 to achieve the desired effect. Alternatively, an elastic film is used as the elastic members 61, 62 for the front and rear sheet members wherein width and/or thickness of the elastic members 61 of the front sheet member 20 may be differentiated from those of the elastic members 62 for the rear sheet member 30 to achieve the desired effect.

As still another method causing the front sheet member to contract more significantly than the rear sheet member 30, the step of making the elastic members 62 bonded to the rear sheet member 30 inelastic may be provided. The elastic members 62 for the rear sheet member 30 can be made inelastic by the method of prior art, for example, cutting, heat treating or chemically treating the elastic members 62.

The invention claimed is:

1. A method of making disposable diapers, comprising the steps of:
    forming front and rear sheet members by
        continuously feeding a web for forming a front sheet member and a web for forming a rear sheet member;
        continuously feeding elastic members for the front and rear sheet members under tension in a first machine direction extending in a straight line;
        bonding said elastic members to the corresponding webs of said front and rear sheet members, over an approximately half width of each of said webs as viewed in a first cross direction orthogonal to the first machine direction; and
        folding each of said webs to sandwich said elastic members to obtain said front sheet member and said rear sheet member, said front sheet member having a constant width dimension as measured in the first cross direction and said rear sheet member having a constant width dimension so that said front and rear sheet members continuously run in the first machine direction while being spaced from each other in the first cross direction;
    continuously feeding, at regular intervals and to said front and rear sheet members running in the first machine direction, absorbent panels in a second machine direction opposite to the first machine direction, each of the absorbent panels including
        (i) a pair of crotch region elastic members for a crotch region along opposite long sides of the absorbent panel and bonded under tension thereto, and (ii) an absorbent core bonded thereto and symmetric about an imaginary center line bisecting a distance between said pair of crotch region elastic members;

after said folding, placing and bonding said absorbent panel directly on and to top surfaces of said front and rear sheet members so that said pair of crotch region elastic members extends orthogonally to said elastic members for the front sheet member and said elastic members for the rear sheet member; and cutting said front and rear sheet members having said absorbent panels bonded thereto substantially along the middle between each pair of said adjacent absorbent panels in the first machine direction to obtain individual diapers, wherein the step of continuously feeding the absorbent panels further comprises feeding said crotch region elastic members continuously extending from one absorbent panel to another absorbent panel in the second machine direction.

2. The method according to claim 1, wherein
the step of continuously feeding the absorbent panels further comprises
continuously feeding a liquid-pervious sheet and a liquid-impervious sheet in the second machine direction and feeding said absorbent core at regular intervals so as to be symmetric about said imaginary center line bisecting the distance between said pair of crotch region elastic members, and the method further comprises
bonding said crotch region elastic members under tension to at least one of said liquid-pervious sheet and said liquid-impervious sheet, and bonding said absorbent core between said liquid-pervious sheet and said liquid-impervious sheet; and cutting said liquid-pervious sheet and said liquid-impervious sheet substantially along the middle between each pair of the adjacent absorbent cores in a second cross direction orthogonal to said second machine direction to obtain individual absorbent panels.

3. The method according to claim 1, wherein said step of forming the front and rear sheet members comprises the step of bonding said elastic members for the front sheet member and said elastic members for the rear sheet member to the corresponding webs under tension, so that said front sheet member contract more than said rear sheet member when said elastic members for said front and rear sheet members, respectively, have tension released.

4. The method according to claim 1, wherein said step of forming the front and rear sheet members comprises the step of adjusting a tensile stress under which said elastic members for the front sheet member are bonded to said front sheet member to be higher than a tensile stress under which said elastic members for the rear sheet member are bonded to said rear sheet member.

5. The method according to claim 1, further comprising the step of making said elastic members for the rear sheet member inelastic at least in a region of said elastic members overlapped by said absorbent core.

6. The method according to claim 1, wherein said step of placing and bonding said absorbent panel comprises the step of bonding said absorbent panel to said front sheet member and said rear sheet member so that a dimension over which said absorbent core overlaps said front sheet member in the first cross direction is larger than a dimension over which said absorbent core overlaps said rear sheet member in first the cross direction.

7. The method according to claim 1, wherein
each of said individual diapers is a pants-type diaper including a front waist region-side belt and a rear waist region-side belt formed by said front and rear sheet members, respectively, said absorbent panel of the individual diaper connects said front and rear waist region-side belts, and opposite side edges of said front waist region-side belt are bonded to opposite side edges of said rear waist region-side belt.

8. The method according to claim 1, further comprising the steps of:
cutting said front and rear sheet members while said front and rear waist sheet members are spaced away from each other in the first cross direction to obtain a front waist region-side belt and a rear waist region-side belt of each of the individual diapers, wherein said absorbent panel of each of the individual diapers connects said front and rear waist region-side belts, providing a fastener including (i) a hook member and a corresponding loop member or (ii) a pressure-sensitive adhesive tape and a corresponding target tape, on opposite side edges of the front waist region-side belt and on opposite side edges of the rear waist region-side belt, and connecting the front and rear waist region-side belts of each of the individual diapers together by the fastener.

9. The method according to claim 8, wherein the step of cutting the front and rear sheet members is performed before the step of connecting the front and rear waist region-side belts.

10. The method according to claim 8, wherein the step of placing and bonding said absorbent panel is performed before the step of providing the fastener and the step of connecting the front and rear waist region-side belts.

11. The method according to claim 1, further comprising the step of defining an imaginary cut line along which the front and rear sheet members will be cut, wherein the step of defining the imaginary cut line is performed after the step of placing and bonding said absorbent panel.

12. The method according to claim 1, wherein said step of forming the front and rear sheet members comprises
the step of adjusting a tensile stress under which said elastic members for the front sheet member are bonded to said front sheet member to be higher than a tensile stress under which said elastic members for the rear sheet member are bonded to said rear sheet member, so that a dimension of the absorbent panel in the vicinity of a boundary line between the absorbent panel and the front sheet member is smaller than a dimension of the absorbent panel in the vicinity of a boundary line between the absorbent panel and the rear sheet member when said elastic members for said front and rear sheet members, respectively, have tension released.

13. The method according to claim 1, wherein the elastic members for the front sheet member and the elastic members for the rear sheet member are fed continuously along the straight line before said placing and bonding said absorbent panel directly on and to said top surfaces of said front and rear sheet members.

14. The method according to claim 1, wherein at said cutting, said front and rear sheet members are disposed opposite to each other in the first cross direction.

15. The method according to claim 1, wherein at said step of continuously feeding, the elastic members for the front sheet member and the elastic members for the rear sheet member extend continuously along the straight line before said step of cutting said front and rear sheet members.

16. The method according to claim 1, wherein at said step of folding, each of said webs is folded in half in the first cross direction so that side edges of each of said webs are flush with each other.

17. The method according to claim 1, wherein at the step of forming the front and rear sheet members, the elastic members for the front sheet member and the elastic members for the rear sheet member are fed continuously along the straight line.

18. A method of making disposable diapers, comprising the steps of:

forming front and rear sheet members by continuously feeding a web for forming a front sheet member and a web for forming a rear sheet member;

continuously feeding elastic members for the front and rear sheet members under tension in a first machine direction;

bonding said elastic members to the corresponding webs of said front and rear sheet members, over an approximately half width of each of said webs as viewed in a first cross direction orthogonal to the first machine direction; and folding each of said webs to sandwich said elastic members to obtain said front sheet member and said rear sheet member, said front sheet member having a constant width dimension as measured in the first cross direction and said rear sheet member having a constant width dimension so that said front and rear sheet members continuously run in the first machine direction while being spaced from each other in the first cross direction;

continuously feeding, at regular intervals and to said front and rear sheet members running in the first machine direction, absorbent panels in a second machine direction, each of the absorbent panels including (i) a pair of crotch region elastic members for a crotch region along opposite long sides of the absorbent panel and bonded under tension thereto, and (ii) an absorbent core bonded thereto and symmetric about an imaginary center line bisecting a distance between said pair of crotch region elastic members;

after said folding, placing and bonding said absorbent panel directly on and to top surfaces of said front and rear sheet members so that said pair of crotch region elastic members extends orthogonally to said elastic members for the front sheet member and said elastic members for the rear sheet member; and cutting said front and rear sheet members having said absorbent panels bonded thereto substantially along the middle between each pair of said adjacent absorbent panels in the first machine direction to obtain individual diapers.

\* \* \* \* \*